(12) United States Patent
Youker et al.

(10) Patent No.: US 7,719,854 B2
(45) Date of Patent: May 18, 2010

(54) INTEGRATED ELECTROMAGNETIC INTERFERENCE FILTERS AND FEEDTHROUGHS

(75) Inventors: Nick A. Youker, River Falls, WI (US); Lawrence D. Swanson, Lino Lakes, MN (US); John E. Hansen, Coon Rapids, MN (US); William J. Linder, Golden Valley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 578 days.

(21) Appl. No.: 10/632,138

(22) Filed: Jul. 31, 2003

(65) Prior Publication Data

US 2005/0024837 A1 Feb. 3, 2005

(51) Int. Cl.
 H05K 7/02 (2006.01)
 H05K 7/06 (2006.01)
 H05K 7/08 (2006.01)
 H05K 7/10 (2006.01)
(52) U.S. Cl. .................. 361/782; 361/763; 361/794
(58) Field of Classification Search ......... 361/760–766, 361/301–302; 333/180–185; 174/17.05–18
See application file for complete search history.

(56) References Cited

U.S. PATENT DOCUMENTS

| | | | |
|---|---|---|---|
| 4,152,540 A | 5/1979 | Duncan et al. | |
| 4,525,766 A | 6/1985 | Peterson | |
| 4,536,820 A | 8/1985 | Binder et al. | |
| 4,678,868 A | 7/1987 | Kraska et al. | |
| 4,784,618 A | 11/1988 | Sakamoto et al. | |
| 4,934,366 A | 6/1990 | Truex et al. | |
| 4,991,582 A * | 2/1991 | Byers et al. ............. | 607/2 |
| 4,995,834 A | 2/1991 | Hasegawa | |
| 5,023,577 A | 6/1991 | Drake | |
| 5,041,900 A | 8/1991 | Chen et al. | |
| 5,070,314 A * | 12/1991 | Decker .................. | 333/260 |
| 5,153,539 A | 10/1992 | Hara et al. | |
| 5,163,428 A | 11/1992 | Pless | |
| 5,175,067 A | 12/1992 | Taylor et al. | |
| 5,213,522 A | 5/1993 | Kojima | |
| 5,333,095 A | 7/1994 | Stevenson et al. | |
| 5,336,242 A | 8/1994 | Zadeh | |

(Continued)

OTHER PUBLICATIONS

"U.S. Appl. No. 10/119,543 Final Office Action Jul. 18, 2005".

(Continued)

*Primary Examiner*—Tuan T Dinh
(74) *Attorney, Agent, or Firm*—Schwegman, Lundberg & Woessner, P.A.

(57) ABSTRACT

An assembly integrating commercially available capacitors into filtered feedthroughs. A feedthrough assembly comprises a plurality of Input/Output (I/O) conductors, wherein the I/O conductors pass through a hermetic seal such that a first end of the I/O conductors reside on a non-hermetic side of the hermetic seal and a second end of the I/O conductors reside on a hermetic side of the hermetic seal, a printed circuit interconnect substrate residing on the hermetic side of the hermetic seal, and a plurality of ceramic chip capacitors mounted on the printed circuit interconnect substrate, wherein a first end of each capacitor is connected via the interconnect to the second end of an I/O conductor and a second end of each capacitor is connected via the interconnect to a constant voltage level.

26 Claims, 6 Drawing Sheets

U.S. PATENT DOCUMENTS

| | | | |
|---|---|---|---|
| 5,406,444 A | | 4/1995 | Selfried et al. |
| 5,620,476 A | | 4/1997 | Truex et al. |
| 5,650,759 A | | 7/1997 | Hittman et al. |
| 5,658,319 A | | 8/1997 | Kroll |
| 5,683,434 A | | 11/1997 | Archer |
| 5,683,435 A | * | 11/1997 | Truex et al. .................. 607/37 |
| 5,782,891 A | * | 7/1998 | Hassler et al. ................ 607/36 |
| 5,817,130 A | | 10/1998 | Cox et al. |
| 5,851,222 A | | 12/1998 | Taylor et al. |
| 5,867,361 A | | 2/1999 | Wolf et al. |
| 5,870,272 A | | 2/1999 | Seifried et al. |
| 5,871,513 A | | 2/1999 | Taylor et al. |
| 5,896,267 A | * | 4/1999 | Hittman et al. ............. 361/302 |
| 5,905,627 A | | 5/1999 | Brendel et al. |
| 5,999,398 A | | 12/1999 | Maki et al. |
| 6,008,980 A | | 12/1999 | Stevenson et al. |
| 6,031,710 A | | 2/2000 | Wolf et al. |
| 6,044,300 A | | 3/2000 | Gray |
| 6,076,017 A | | 6/2000 | Taylor et al. |
| 6,090,503 A | | 7/2000 | Taylor et al. |
| 6,529,103 B1 | * | 3/2003 | Brendel et al. .............. 333/182 |
| 6,657,133 B1 | * | 12/2003 | Chee ........................ 174/260 |
| 6,657,849 B1 | * | 12/2003 | Andresakis et al. ......... 361/311 |
| 6,778,040 B2 | * | 8/2004 | Kim ........................... 333/182 |
| 2003/0139096 A1 | * | 7/2003 | Stevenson et al. ........... 439/620 |
| 2003/0191505 A1 | | 10/2003 | Gryzwa et al. |

OTHER PUBLICATIONS

"U.S. Appl. No. 10/119,543 Final Office Action Aug. 24, 2006".
"U.S. Appl. No. 10/119,543 Non-Final Office Action Dec. 13, 2004".
"U.S. Appl. No. 10/119,543 Non-Final Office Action Feb. 7, 2006".
"U.S. Appl. No. 10/119,543 Response to Final Office Action Nov. 18, 2005".
"U.S. Appl. No. 10/119,543 Response to Non-Final Office Action May 13, 2005".
"U.S. Appl. No. 10/119,543 Response to Non-Final Office Action Jun. 7, 2006".
"U.S. Appl. No. 10/119,543 Final Office Action mailed Jul. 18, 2005", 7 pgs.
"U.S. Appl. No. 10/119,543 Final Office Action mailed Aug. 24, 2006", 10 pgs.
"U.S. Appl. No. 10/119,543 Non Final Office Action mailed Feb. 7, 2006", 12 pgs.
"U.S. Appl. No. 10/119,543 Non Final Office Action mailed Dec. 13, 2004", 6 pgs.
"U.S. Appl. No. 10/119,543 Response filed May 13, 2005 to Non Final Office Action mailed Dec. 13, 2004", 7 pgs.
"U.S. Appl. No. 10/119,543 Response filed Jun. 7, 2006 to Non Final Office Action mailed Feb. 7, 2006", 8 pgs.
"U.S. Appl. No. 10/119,543 Response filed Nov. 18, 2005 to Final Office Action mailed Jul. 18, 2005", 7 pgs.

* cited by examiner

INTEGRATED ELECTROMAGNETIC INTERFERENCE FILTERS AND FEEDTHROUGHS

TECHNICAL FIELD

This patent application relates to implantable medical devices and, in particular, to hermetic seal feedthroughs and electromagnetic interference filters integrated into one or more assemblies.

BACKGROUND

Implantable medical devices generally include a hermetically sealed metal case or can. For implantable cardiac rhythm management devices, electrical signals sensed in the body and electrical signals delivered to the body need to pass through the hermetic seal. These electrical signals must pass through the hermetic seal of the device and yet be insulated from the metal case. This is accomplished with feedthroughs. Feedthroughs are comprised of an electrical conductor, usually a pin, passing through insulating material and providing connection from circuitry internal to the can to a point external to the can while maintaining the hermetic seal.

Electromagnetic signals from external electrical sources encountered in a patient's normal environment can also pass through the feedthrough and interfere with proper operation of the implantable device. Consequently, electromagnetic interference (EMI) filters are provided to prevent unwanted electromagnetic signals from being sensed by the device and interfering with its normal operation. For cardiac rhythm management devices these filters must be designed to withstand electrical signals of several hundred volts that can be encountered during electrocautery, external defibrillation or internal defibrillation if the device is an implantable defibrillator. Also, the filters must also be located as close as possible to the hermetic seal to prevent or minimize entry of the signals into the metal case.

Often, the EMI filters are comprised of capacitors provided with the feedthroughs as a custom designed assembly. The assemblies are extremely costly due to the complex processes required in their manufacture. Also, interconnecting the custom filtered feedthroughs and the rest of the assemblies in the device are often difficult to control effectively. One result is that it is difficult to obtain and maintain sources for the filtered feedthrough. What is needed is an assembly that meets the design challenges required of filtered feedthroughs for medical devices yet reduces cost and increases their availability.

SUMMARY

This document discusses integrating commercially available capacitors into a filtered feedthrough assembly.

The feedthrough assembly comprises a plurality of Input/Output (I/O) conductors passing through a hermetic seal such that a first end of the I/O conductors reside on a non-hermetic side of the hermetic seal and a second end of the I/O conductors reside on a hermetic side of the hermetic seal within a metal case of the apparatus. The assembly also includes a printed circuit interconnect substrate residing on the hermetic side of the hermetic seal and a plurality of ceramic chip capacitors mounted on the printed circuit interconnect substrate. A first end of each capacitor is connected through the substrate to the second end of an I/O conductor and a second end of each capacitor is electrically connected through the substrate to the metal case.

A method of integrating EMI filters and feedthroughs on an implantable medical device comprises forming a hermetic seal around a plurality of Input/Output (I/O) conductors which pass through the hermetic seal. EMI filter circuits are formed using discrete capacitors mounted on a printed circuit substrate. The printed circuit substrate and the EMI filter circuits are mounted on the hermetic side of the hermetic seal, and attached to the I/O conductors.

This summary is intended to provide an overview of the subject matter of the present application. It is not intended to provide an exclusive or exhaustive explanation of the invention. The detailed description is included to provide further information about the subject matter of the present patent application.

DETAILED DESCRIPTION

In the following detailed description, reference is made to the accompanying drawings which form a part hereof, and specific embodiments in which the invention may be practiced are shown by way of illustration. It is to be understood that other embodiments may be used and structural changes may be made without departing from the scope of the present invention.

This document is concerned with materials and methods to create a filtered feedthrough assembly for implantable cardiac rhythm management devices. However, the feedthrough assembly can be generalized to any type of implantable medical devices that needs to pass electrical signals through a hermetic seal.

Figure 1:
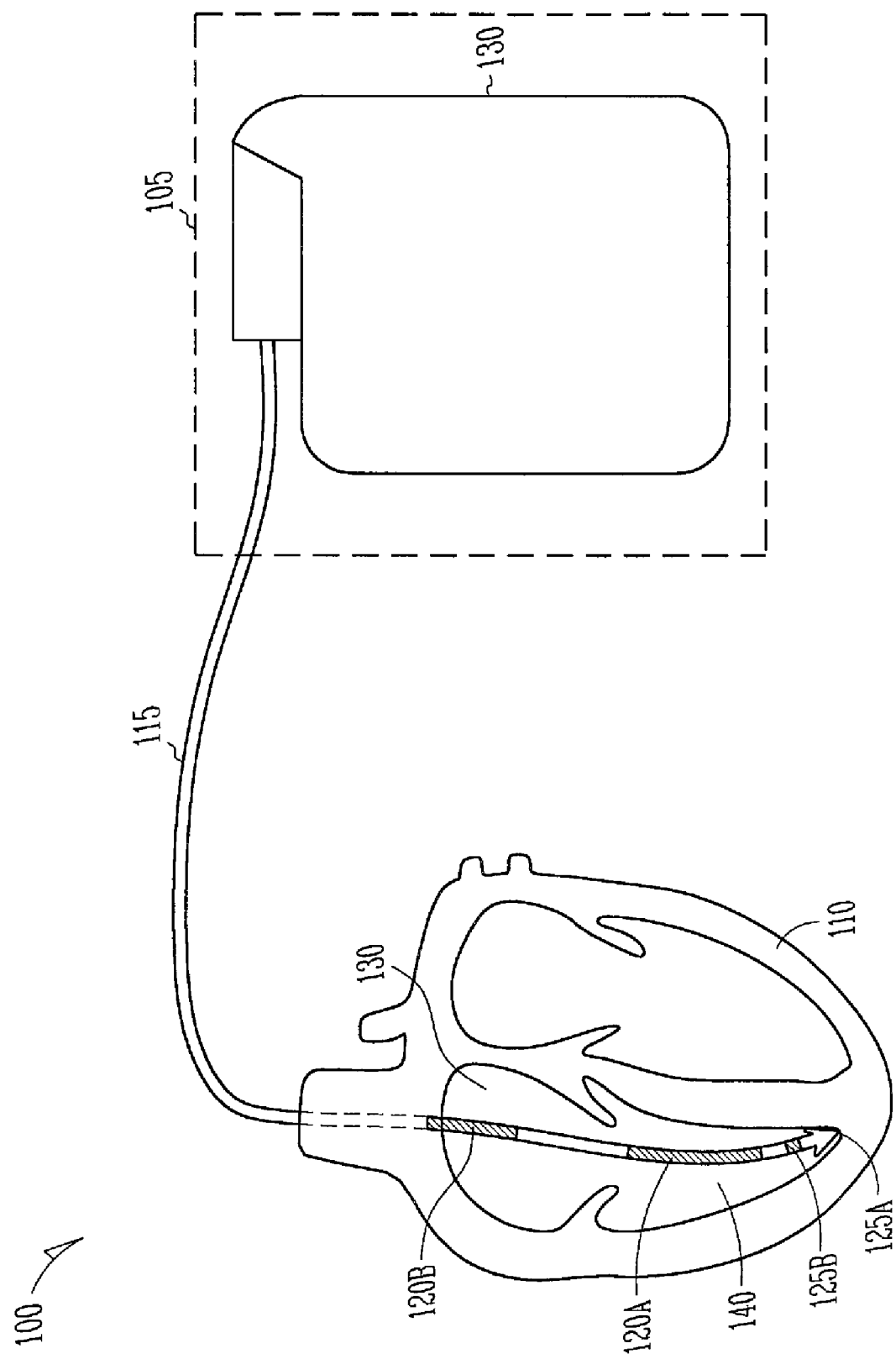
FIG. 1 is a generalized schematic diagram of one embodiment of a portion of a cardiac rhythm management system.

FIG. 1 is a generalized schematic diagram of one embodiment of a system 100 that uses a hermetic seal. The system shown is a portion of a cardiac rhythm management system. Various embodiments of system 100 include external or implantable pulse generators, pacer/defibrillators, cardioverters, defibrillators, any combination of the foregoing, or any other system using or maintaining cardiac rhythms. Further system embodiments include any implantable medical device that requires a hermetic seal, such as neuro-stimulators, insulin pumps, implantable sensors and the like. Yet further embodiments of system 100 include more than one hermetic seal.

In the embodiment of FIG. 1, cardiac rhythm management system 100 includes an implantable pulse generator 105 coupled to heart 110 via one or more endocardial or epicardial leads, such as a pacing lead or a defibrillation lead 115. Defibrillation lead 115 includes one or more defibrillation electrodes, such as for delivering defibrillation counter-shock ("shock") therapy via first defibrillation electrode 120A and/ or second defibrillation electrode 120B. Defibrillation lead 115 may also include additional electrodes, such as for delivering pacing therapy via first pacing electrode 125A (e.g., a "tip" electrode) and/or second pacing electrode 125B (e.g., a "ring" electrode). Defibrillation electrodes 120A-B and pacing electrodes 125A-B are typically disposed in or near one or more chambers of heart 110.

Because the pulse generator 105 is implantable, it includes a hermetic seal. Electrical signals sensed on the lead or leads need to pass through the hermetic seal to communicate with the electronics of the pulse generator 105 that are internal to the metal case 130. Electrical signals originating from the internal electronics for delivery to the heart 110 by the leads also need to pass through the hermetic seal. The system 100 shown is a generalized system. Typically several electrical signals pass through the hermetic seal.

Figure 2A:
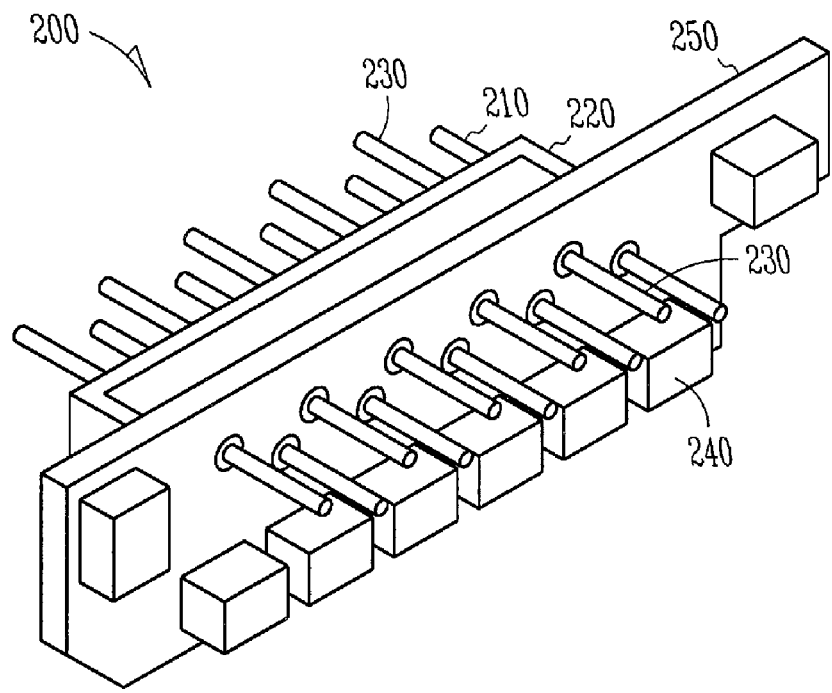
FIG. 2A is a drawing of one embodiment of the filtered feedthrough assembly.

FIG. 2A shows an embodiment of a filtered feedthrough assembly 200. A hermetic seal is formed by a hermetic layer 210 surrounded by a metal plate 220. The hermetic layer 210 is an electrical insulator as well as a barrier to body fluids. In one embodiment, the hermetic layer 210 includes ceramic. In another embodiment, the hermetic layer 210 includes glass. In another embodiment, the hermetic layer includes epoxy. In another embodiment, the metal plate 220 includes titanium. In a further embodiment, the metal plate 220 includes tantalum. Feedthroughs are provided by input/output (I/O) conductors 230 passing through the hermetic layer 210. In one embodiment, the conductors are pins. In another embodiment, the conductors are wires. In a variation of this embodiment, the wires are plated with a metal such as gold. In a further embodiment, the conductors 230 passing through the hermetic layer 210 are conductive metal traces on a printed circuit interconnect that accommodates surface mounting of electronic components. In a variation of this embodiment, the conductive traces are included on a printed circuit board. In another variation of this embodiment, the conductive traces are on a flex circuit substrate. In further embodiments, the conductive traces are formed by etching or deposition on substrates or printed circuit boards. Other variations of combinations of methods of forming the traces with variations of substrates are within contemplation of this application.

Figure 2B:
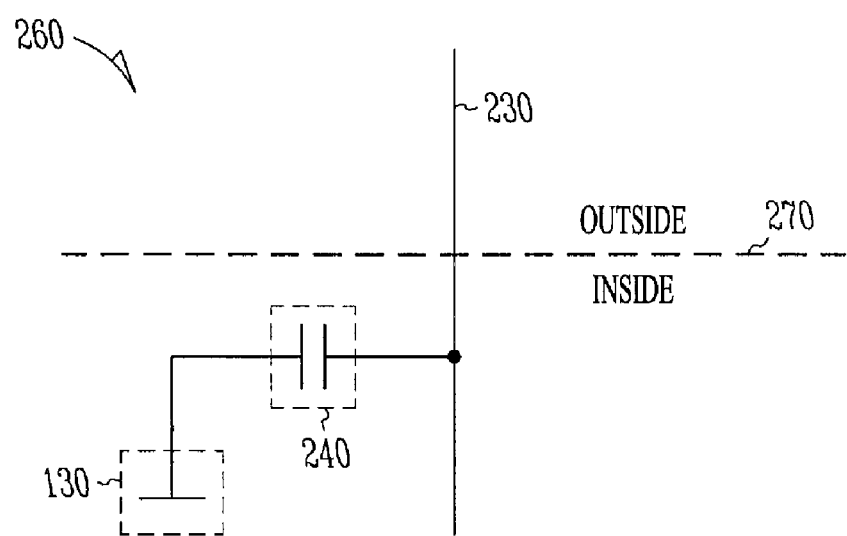
FIG. 2B shows a schematic of an electromagnetic interference filter.

The feedthroughs are filtered with EMI filters. A schematic 260 of the filters is shown in FIG. 2B. The filters comprise a capacitor 240 connected in series from each feedthrough pin or I/O conductor 230 and terminated to the metal case 130. The connection of the I/O conductor 230 to the capacitive filter is made as close as possible to the inside of the hermetic seal 270. The cut-off frequency of the low pass filter is determined by the size of the capacitor 240. In one embodiment, the value of the capacitor 240 is about 1500 pico-farads. In another embodiment, the value of the capacitor 240 is within a range of about 1000 to 2000 pico-farads.

Figure 3:
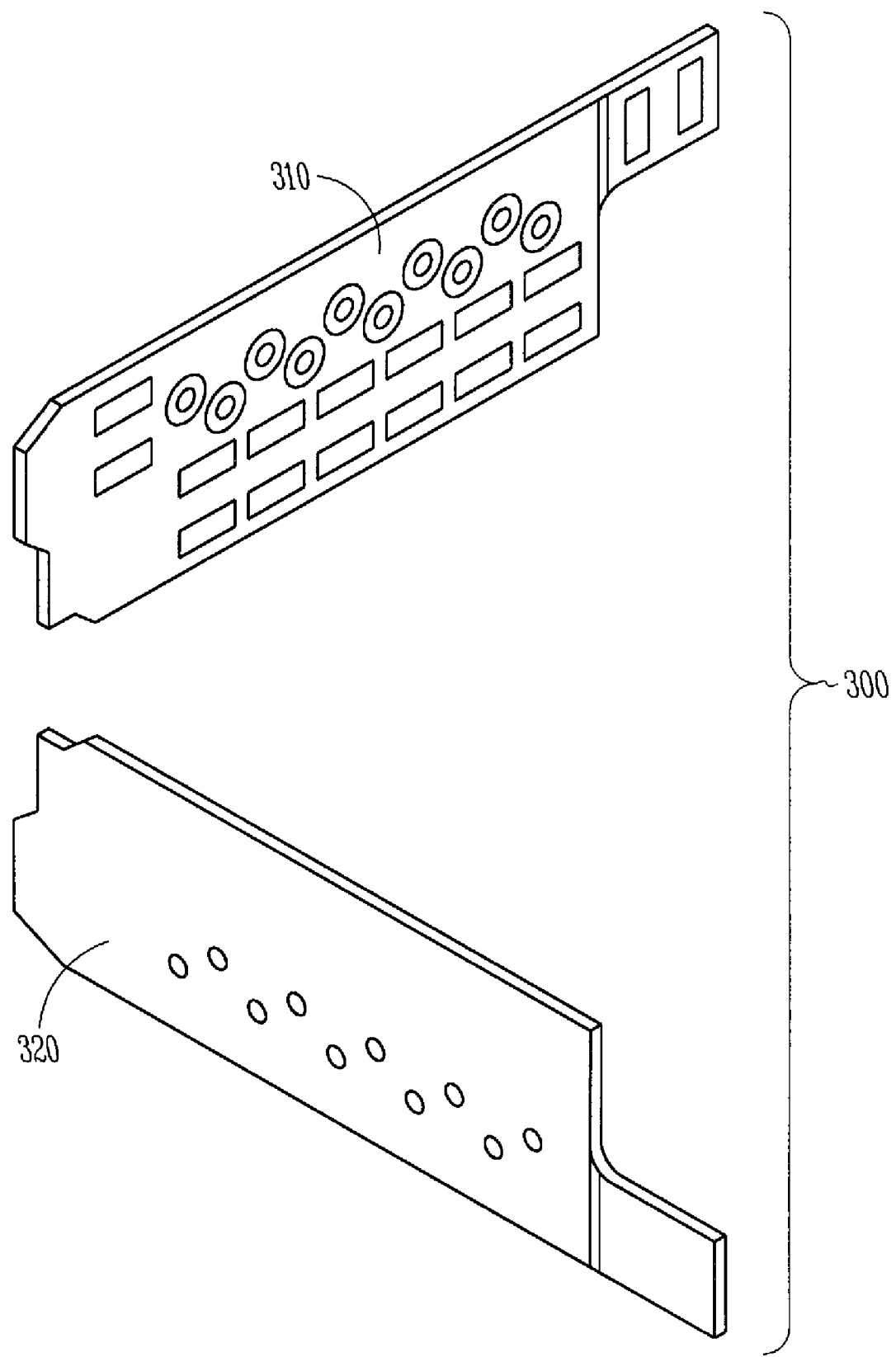
FIG. 3 is a drawing of a printed circuit board used in the assembly.

To form the EMI filters, multiple, commercially available, discrete capacitors 240 are mounted on a printed circuit substrate. One embodiment of a printed circuit substrate 300 is shown in FIG. 3. The embodiment shown is a substrate 300 for a ten-conductor feedthrough. A front view 310 and a back view 320 are shown. In one embodiment, substrate 300 is a multi-layer printed circuit board (PCB) comprising a material commonly used in PCB manufacturing such as, for example, FR4, G10 and their equivalents. In another embodiment, the PCB material includes a ceramic. In yet another embodiment, substrate 300 is flexible circuit tape comprising a material such as polyimide.

Figure 4:
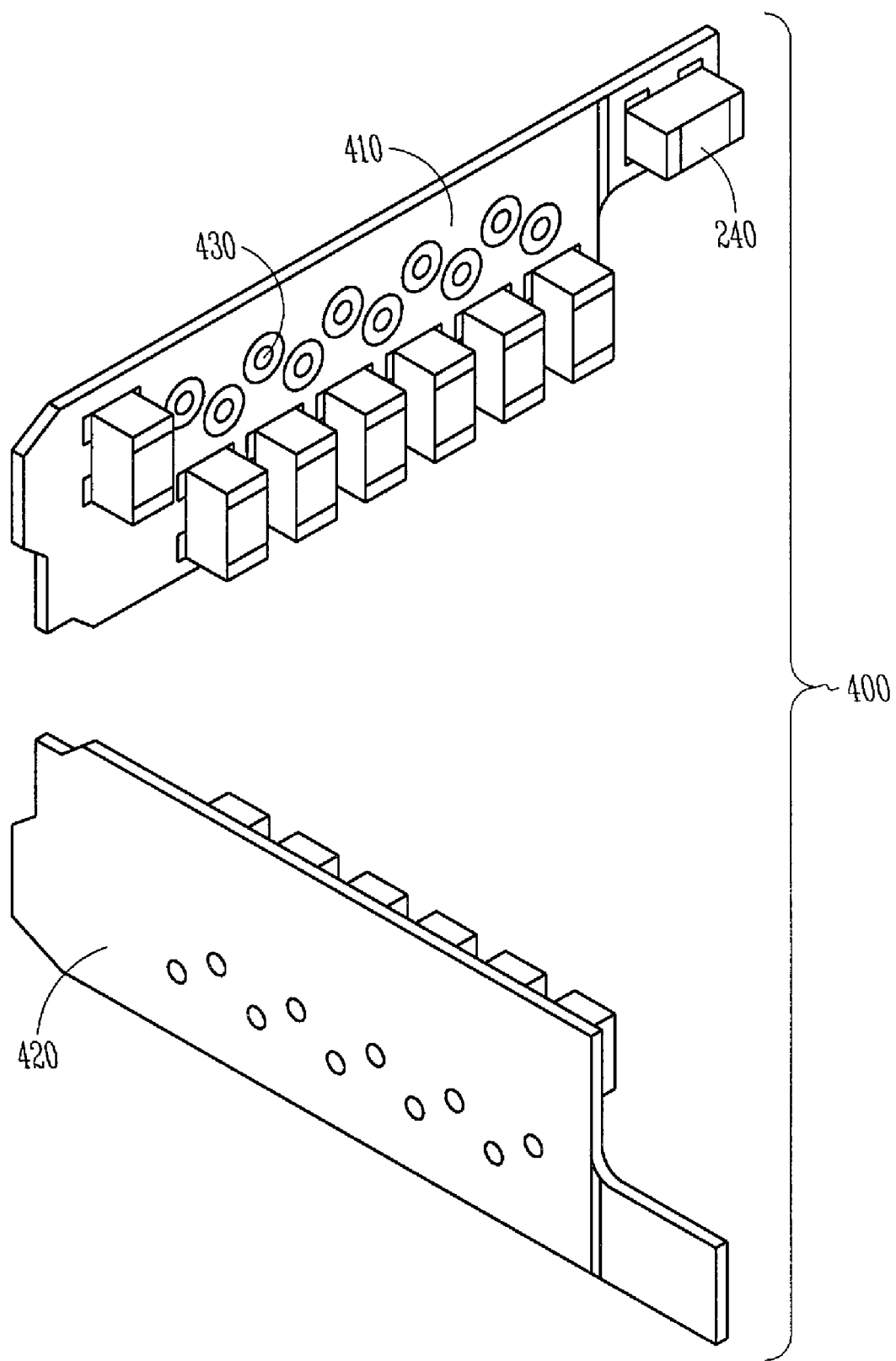
FIG. 4 is a drawing of a printed circuit board populated with electromagnetic interference filter capacitors.

FIG. 4 shows an embodiment of a substrate sub-assembly 400 that includes capacitors 240. A front view 410 and a back view 420 are shown. The sub-assembly 400 is then mounted to the hermetic side of the feedthrough and hermetic seal assembly with the front side 410 pointing into the hermetically sealed interior of the medical device. I/O conductors 230 are positioned through the holes 430 of the substrate 300. The substrate 300 provides the interconnection between the capacitors 240 and the I/O conductors 230. The connections to the I/O conductors 230 are made using an electrically conductive medium such as solder or electrically conductive epoxy. The substrate 300 also provides a connection from the capacitors 240 to the metal case 130 to form the filters.

In one embodiment, the capacitors 240 have a breakdown voltage of about 1200 volts to provide robustness in an environment exposed to defibrillation or electrocautery voltages. In another embodiment, the capacitors have a breakdown voltage that falls within a range of about 200 to 1500 volts. In one embodiment the capacitors 240 are individually packaged chip capacitors. In another embodiment, the chip capacitors include surface mount packages. In yet another embodiment, the capacitors 240 are in multi-chip packages.

EMI filters are most effective if the interfering electrical signals are filtered immediately as they enter the hermetic side of an implantable device and minimize any EMI entering the sealed can. Thus it is important to keep the length of traces from the seal to the filters as short as possible to maximize EMI protection. Also, it is important to minimize any parasitic inductance of the interconnect to avoid cross-talk among the signals that need to pass through the hermetic seal.

One method to minimize the amount of interconnect is to use a multi-layer circuit board for the printed circuit substrate 300. A multi-layer circuit board provides flexibility in layout of the signal and via layers and placement of the discrete capacitors. This flexibility allows the capacitors 140 to be placed as close as possible to the I/O conductors 230. In one embodiment, the capacitors are surface mounted to the substrate 300. In another embodiment, the capacitors are wire-bonded to the substrate. Using a multi-layer circuit board with layers, or planes, of constant voltage levels, such as ground planes, minimizes trace lengths and any parasitic inductance of circuit interconnections. Also, use of the voltage planes adds to interconnect robustness in the high voltage environments discussed previously. The signal traces of the signal layer can be sized to withstand the high spike currents that can occur in such environments and the ground planes provide a robust termination of the high voltage signals. In one embodiment, the EMI filters are placed on the same circuit substrate as the main electronic components of the system 100. In another embodiment, the EMI filters are placed on a separate circuit substrate 300. Placing the EMI filters on a second circuit substrate provides flexibility in placing the filters as close as possible to the hermetic seal 270.

Figure 5A:
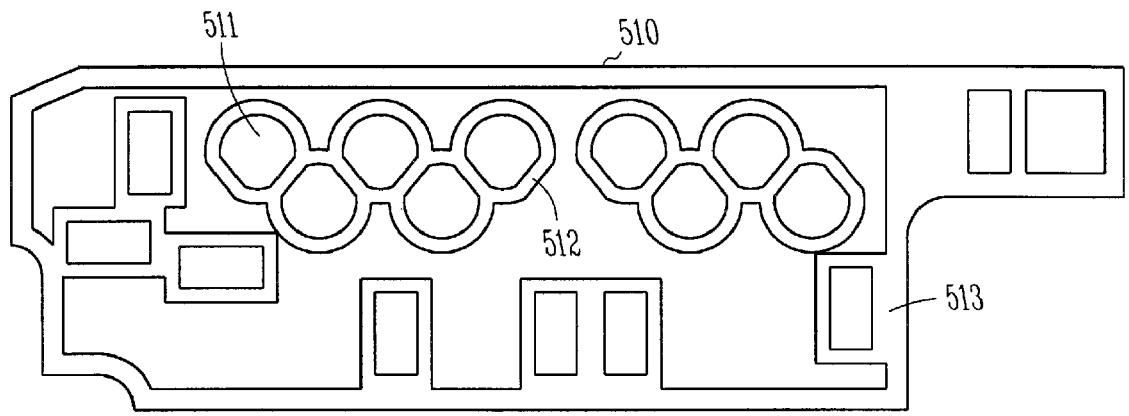
FIG. 5A-C are embodiments of layers of a multi-layer printed circuit board.
Figure 5B:
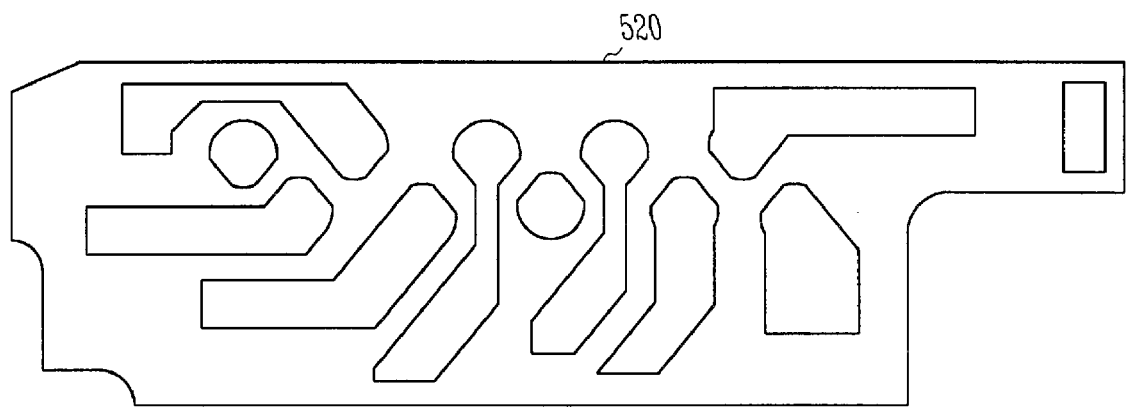
Figure 5C:
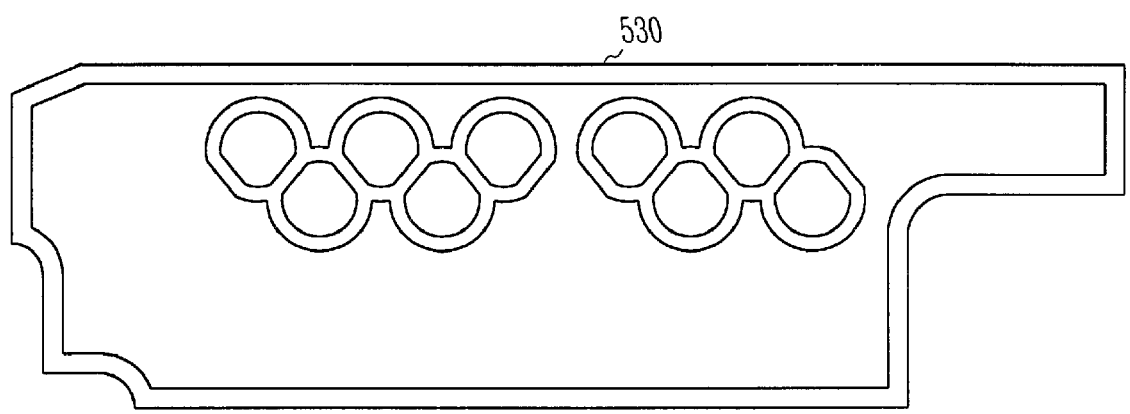

FIG. 5A-5C show the layers of one embodiment of a multilayer board for a ten-conductor feedthrough. Various embodiments containing different numbers of conductors or pins and layers are within contemplation of the present application. Layer one 510, shown in FIG. 5A, is a ground layer. Throughout the layer views, the dark areas represent metal 514 deposited on the substrate 300. The layer 510 shows that when holes 430 are formed in the substrate 300, the metal layout isolates nine of the pin locations 511 from the ground layer 510 while one pin location 512 will be connected to ground. The layer 510 also contains pad locations 513 for one end of capacitors 240. The other end of the capacitors is electrically connected to the case 130. FIG. 5B shows that layer two 520 is a signal, or interconnect, layer. When holes 430 are formed in the substrate (for example by drilling) and the pins are inserted, the metal 514 in the signal layer connects the pins to the side of the capacitors not connected to the case 130. Thus, in the embodiment shown, the pins 230 are routed by metal 514, 522 to a capacitor 240 and then to the case 130 to form the EMI filters.

FIG. 5C shows that layer three 530 is a ground layer. Layer three is the bottom-most layer and faces the hermetic seal when the feedthrough assembly 200 is formed.

Minimizing the thickness of the substrate 200 is also a factor in keeping the filters near the I/O conductors 230. In one embodiment, the thickness of the substrate 200 without the solder mask is less than about thirteen thousandths of an inch. The capacitors 140, the technology used for the interconnection and the processes used to build the hermetic seal are commercially available. This increases the number of vendors available to supply parts and reduces the cost of the assembly 100.

Figure 6:
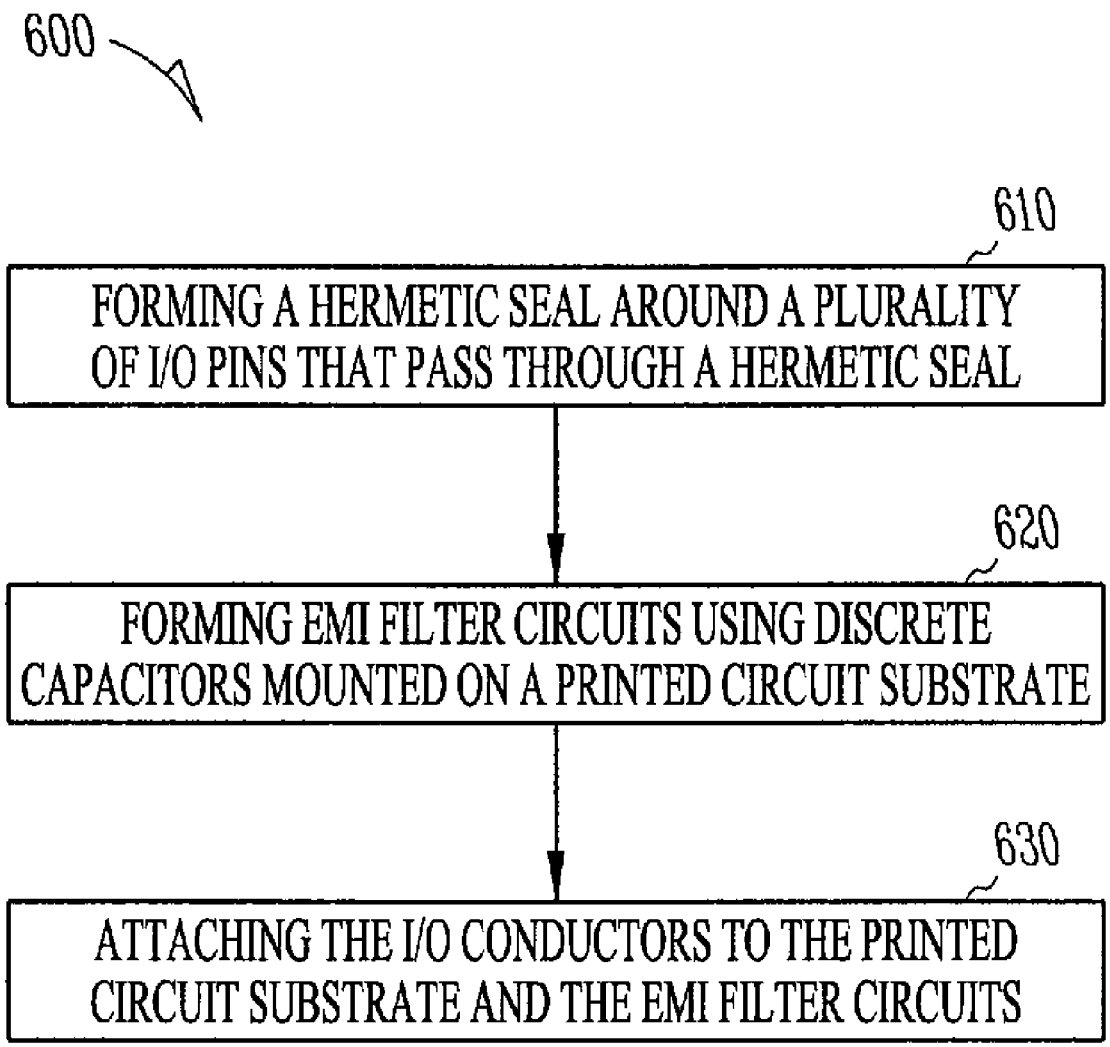
FIG. 6 shows a method of integrating electromagnetic interference (EMI) filters and feedthroughs in an implantable medical device.

FIG. 6 shows a method 600 of integrating electromagnetic interference (EMI) filters and feedthroughs in an implantable medical device. At 610, a hermetic seal is formed around a plurality of Input/Output (I/O) conductors that pass through the hermetic seal. At 620, EMI filter circuits are formed using discrete capacitors mounted on a printed circuit substrate. At 630, the I/O conductors are attached to the printed circuit substrate and the EMI filter circuits. In one embodiment, the printed circuit substrate is the same substrate for the main electrical components of the system 100. In another embodiment, the printed circuit substrate is separate substrate from the main electronics substrate of the system. In yet another embodiment of the method, the printed circuit substrate and the EMI filter circuits are mounted on the hermetic side of the hermetic seal.

Although specific examples have been illustrated and described herein, it will be appreciated by those of ordinary skill in the art that any arrangement calculated to achieve the same purpose could be substituted for the specific example shown. This application is intended to cover any adaptations or variations of the present invention. Therefore, it is intended that this invention be limited only by the claims and their legal equivalents.

What is claimed is:

1. An apparatus comprising:
one or more Input/Output (I/O) conductors, wherein the I/O conductors pass through a hermetic seal such that a first end of the I/O conductors resides on a non-hermetic side of the hermetic seal and a second end of the I/O conductors resides on a hermetic side of the hermetic seal within a hermetically sealed interior of a hermetically sealed metal case of the apparatus;
a printed circuit interconnect substrate residing on the hermetic side of the hermetic seal, wherein the printed circuit interconnect substrate includes a multi-layer circuit board comprising a buried signal layer between first and second conductive layers, wherein each conductive layer is electrically connected to a constant voltage to form a constant voltage plane, wherein the multi-layer circuit board is arranged substantially parallel to the hermetic seal and normal to the I/O conductors to provide electrical shielding, and wherein one I/O conductor provides an electrical connection to the constant voltage plane; and
one or more ceramic chip capacitors mounted on the printed circuit interconnect substrate and mounted within the hermetically sealed interior of the hermetically sealed metal case, wherein a first end of each capacitor is electrically connected via printed circuit interconnect to the second end of an I/O conductor and a second end of each capacitor is electrically connected via the printed circuit interconnect to the metal case.

2. The apparatus of claim 1, wherein the printed circuit interconnect substrate is mounted on the hermetic side of the hermetic seal.

3. The apparatus of claim 1, wherein the printed circuit interconnect substrate includes a printed circuit board material.

4. The apparatus of claim 1, wherein the printed circuit interconnect substrate includes flexible circuit tape.

5. The apparatus of claim 1, wherein the printed circuit interconnect substrate is a multi-layer substrate.

6. The apparatus of claim 1, wherein the printed circuit interconnect substrate includes an electrically conductive medium.

7. The apparatus of claim 1, wherein the capacitors have a dielectric breakdown voltage of about 1200 volts.

8. The apparatus of claim 1, wherein the capacitors have a dielectric breakdown voltage within a range of about 200 to 1500 volts.

9. The apparatus of claim 1, wherein the capacitors are discrete capacitors.

10. The apparatus of claim 1, wherein the capacitors are included in a multi-chip package.

11. The apparatus of claim 1, wherein the capacitors are adapted to filter electromagnetic interference.

12. The apparatus of claim 1, wherein the hermetic seal is part of an implantable medical device.

13. The apparatus of claim 1, wherein the I/O conductors are pins.

14. The apparatus of claim 1 wherein the I/O conductors are wires.

15. The apparatus of claim 1 wherein the I/O conductors are conductive traces.

16. The apparatus of claim 3, wherein the printed circuit board material includes a ceramic.

17. The apparatus of claim 3, wherein the printed circuit board material includes FR4.

18. The apparatus of claim 4, wherein the flexible circuit tape includes polyimide.

19. The apparatus of claim 6, wherein the electrically conductive medium includes solder.

20. The apparatus of claim 6, wherein the electrically conductive medium includes conductive epoxy.

21. The apparatus of claim 6, wherein the electrically conductive medium includes wire-bonds.

22. The apparatus of claim 9, wherein the capacitors include surface mount packaging.

23. The apparatus of claim 12, wherein the hermetic seal includes a ceramic.

24. The apparatus of claim 12, wherein the hermetic seal includes an epoxy.

25. The apparatus of claim 12, wherein the hermetic seal includes a glass.

26. The apparatus of claim 15, wherein the conductive traces are included in a printed circuit interconnect that accommodates surface mounting of electronic components.

* * * * *